(12) United States Patent
Shiozaki

(10) Patent No.: US 7,833,747 B2
(45) Date of Patent: Nov. 16, 2010

(54) METHODS FOR DETECTING AN ENDOTOXIN WITH A LYSATE REAGENT

(75) Inventor: Tetsuya Shiozaki, Edogawa-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 201 days.

(21) Appl. No.: 11/914,843

(22) PCT Filed: May 30, 2006

(86) PCT No.: PCT/JP2006/310780

§ 371 (c)(1),
(2), (4) Date: Nov. 19, 2007

(87) PCT Pub. No.: WO2006/129662

PCT Pub. Date: Dec. 7, 2006

(65) Prior Publication Data

US 2009/0076054 A1  Mar. 19, 2009

(30) Foreign Application Priority Data

May 30, 2005  (JP)  ............... 2005-157345

(51) Int. Cl.
*C12Q 1/04* (2006.01)
(52) U.S. Cl. .......................... 435/34; 435/24
(58) Field of Classification Search ............... 435/34, 435/24
See application file for complete search history.

(56) References Cited

U.S. PATENT DOCUMENTS

| | | | |
|---|---|---|---|
| 4,038,029 A | 7/1977 | Teller et al. | |
| 4,273,557 A | 6/1981 | Juranas | |
| 5,346,889 A * | 9/1994 | Tsuchiya et al. | ............... 514/21 |
| 5,917,022 A * | 6/1999 | Davies | ................. 530/390.1 |

FOREIGN PATENT DOCUMENTS

| | | |
|---|---|---|
| EP | 0 731 354 A1 | 9/1996 |
| JP | 52-90990 | 7/1977 |
| JP | 7 151760 | 6/1995 |
| JP | EP 0 731 354 A1 * | 9/1996 |
| WO | 95 14932 | 6/1995 |

OTHER PUBLICATIONS

Asakawa, Sadao et al., "Application of the Limulus Test for Practical Quality Control on Endotoxin Content in Commercial Human Serum Albumin (HSA) Products. In Comparsion With the Rabbit Pyrogen Test", vol. 114, No. 11, pp. 888 to 893, 1994.
A. M. Cundell, "Use of the Limulus Amebocyte Lysate Endotoxin Assay in Plasma Fractionation.", Progr. Clin. Biol. Res., 1982, vol. 93, pp. 269-280.
Japanese Phamacopoeia Fourteenth Edition, Hirokawa Publishing Co. 2001 B-63 (English Translation) pp. 20-23 w/notes.

* cited by examiner

*Primary Examiner*—Ralph Gitomer
(74) *Attorney, Agent, or Firm*—Oblon. Spivak. McClelland. Maier & Neustadt. L.L.P.

(57) ABSTRACT

An object of the present invention is to provide a method capable of detecting and quantifying endotoxin in a sample in which endotoxin derived from gram-negative bacteria cannot be accurately detected or quantified by the method described in Commentary of the Japanese Pharmacopoeia Fourteenth Edition, Hirokawa Publishing Co. 2001 B-63. It has been found that the above object can be achieved by performing an endotoxin test using a lysate reagent in which the lysate reagent is added into a sample in the presence of albumin and/or globulin.

24 Claims, No Drawings

METHODS FOR DETECTING AN ENDOTOXIN WITH A LYSATE REAGENT

TECHNICAL FIELD

The present invention relates to an endotoxin test method.

BACKGROUND ART

It has been known that contamination of pyrogen in injection solution may cause symptoms such as pyrexia and chills. In order to prevent contamination with pyrogen, pyrogen test has been conventionally employed in a process for preparation or quality control of injection solution to detect pyrogen. However, the test requires much time and labor and being very complicated (see Non-Patent Document 1).

Pyrogen is known to be mainly composed of endotoxin which constituting the cell wall of gram-negative bacteria. For detection and quantification of endotoxin derived from gram-negative bacteria, there are known endotoxin test methods based on a principle of coagulation of blood corpuscle extracts (lysate) of horseshoe crab (such as *Limulus polyphemus* or *Tachypleus tridentatus*) with endotoxin (see Non-Patent Document 2). Recently, such endotoxin test methods are more often used for detection of pyrogen instead of pyrogen test methods.

[Non-Patent Document 1] Commentary of the Japanese Pharmacopoeia Fourteenth Edition, Hirokawa Publishing Co. 2001 B-493

[Non-Patent Document 2] Commentary of the Japanese Pharmacopoeia Fourteenth Edition, Hirokawa Publishing Co. 2001 B-63

DISCLOSURE OF THE INVENTION

Problems to be Solved by the Invention

The present invention provides a method capable of detecting and quantifying endotoxin in a sample in which endotoxin derived from gram-negative bacteria cannot be accurately detected or quantified by the method described in Non-Patent Document 2.

Means for Solving the Problems

As a result of intensive studies of the present inventors, it has been found that the above problem is solved by performing an endotoxin test using a lysate reagent in which the lysate reagent is added into a sample in the presence of albumin and/or globulin, and the present invention has been completed.

Accordingly, the present invention relates to a novel endotoxin test method and a process for preparing an injection having an endotoxin concentration of less than a specification limit, and also relates to the followings.

(1) An endotoxin test method comprising adding a lysate reagent to a solution or dispersion of a camptothecin derivative, a timiperone or a taxane derivative in the presence of albumin and/or globulin.

(2) The test method according to (1), wherein the albumin and/or globulin is human serum albumin.

(3) The test method according to (1) or (2), wherein the camptothecin derivative is irinotecan hydrochloride.

(4) A process for preparing an injection containing a pharmaceutically active ingredient and having an endotoxin concentration of less than a specification limit, comprising a screening step comprising: adding a lysate reagent to a solution or dispersion of the pharmaceutically active ingredient in the presence of albumin and/or globulin; and assessing the presence or absence of endotoxin.

(5) A process for preparing an injection containing a camptothecin derivative, a timiperone or a taxane derivative and having an endotoxin concentration of less than a specification limit, comprising a screening step comprising: adding a lysate reagent to a solution or dispersion of the camptothecin derivative, the timiperone or the taxane derivative in the presence of albumin and/or globulin; and assessing the presence or absence of endotoxin.

(6) The process according to (4) or (5), wherein the albumin and/or globulin is human serum albumin.

(7) The process according to (5) or (6), wherein the camptothecin derivative is irinotecan hydrochloride.

Effect of the Invention

As is evident from Examples described below, the test method of the present invention makes it possible to detect and quantify endotoxin derived from gram-negative bacteria in a sample in which the endotoxin cannot be accurately detected or quantified by conventional test methods. According to the present invention, preparation and quality control of an injection can be performed without using complicated pyrogen test, and a process for preparing an injection having an endotoxin concentration of less than a specification limit can be provided. Moreover, since pyrogen can be detected without employing a pyrogen test with rabbits, the present invention is desirable from a perspective of animal protection.

BEST MODE FOR CARRYING OUT THE INVENTION

In the present invention, a sample (a solution or dispersion of a pharmaceutically active ingredient) is reacted with a lysate reagent in the presence of albumin and/or globulin, and the reaction between endotoxin in the sample and the lysate reagent is detected and quantified.

Examples of the albumin and/or globulin according to the present invention can include those obtained by purifying or partially purifying blood plasma or blood serum, and substances containing albumin and/or globulin as a component. Of such albumins and globulins, those derived from human blood serum are preferred. Examples of the substances containing albumin and/or globulin as a component can include COHN's fractions, albumin fractions and globulin fractions obtained by electrophoresis, commercially available fresh frozen plasma (e.g., those available from Japanese Red Cross Society), heated human plasma protein (e.g., those available from NIHON PHARMACEUTICAL CO., LTD.), human serum albumin (e.g., those available from Japanese Red Cross Society, Mitsubishi Pharma Corporation, or Baxter Limited) and human immunoglobulin (e.g., those available from Japanese Red Cross Society, Mitsubishi Pharma Corporation, or Baxter Limited). In the present invention, human serum albumin is preferred in view of detection sensitivity of endotoxin.

In the present invention, a subject is a sample in which endotoxin cannot be detected or quantified by conventional test methods. Herein, the usual test method refers to the test method described in Non-Patent Document 2 and test methods substantially similar thereto. The method described in Non-Patent Document 2 is substantially the same as the methods described in the United States Pharmacopeia, the European Pharmacopoeia, JIS and Minimum Requirements for Biological Products. Examples of the subject sample include camptothecin derivatives, timiperone and taxane derivatives. Camptothecin derivatives are derivatives having a camptothecin skeleton and generally known as anticancer agents. Examples of known camptothecin derivatives can include irinotecan hydrochloride, nogitecan hydrochloride, Rubitecan, Lurtotecan, 9-aminocamptothecin and derivatives described in International Publication No. WO98/07727, International Publication No. WO98/015573, International Publication No. WO99/17804, International Publication No. WO99/011646 and Japanese Patent Laid-Open No. 10-72467. Taxane derivatives are derivatives having a baccatin skeleton and generally known as anticancer agents. Examples of known taxane derivatives include paclitaxel, docetaxel hydrate, (−)-(1S,2S,3R,4S,5R,8R,9S,10R,13S)-4-acetoxy-2-benzoyloxy-9,10-[(1S)-2-(dimethylamino)ethylideneoxy]-5,20-epoxy-1-hydroxytax-11-en-13-yl(2R,3S)-3-(tert-butoxycarbonylamino)-3-(3-fluoro-2-pyridyl)-2-hydroxypropionate and derivatives described in Japanese Patent Laid-Open No. 7-149779, National Publication of International Application No. 8-508497, Japanese Patent Laid-Open No. 9-12578 and International Publication No. WO96/01259. Any of the above substances can be used in the endotoxin test method of the present invention, and in the process of the present invention for preparing an injection having endotoxin concentration of less than a specification limit.

In the present invention, when the sample (pharmaceutically active ingredient) is not in the form of a solution or dispersion, it is necessary to prepare a sample in the form of a solution or a dispersion using an appropriate solvent (e.g., test solution for endotoxin test, water for an injection, physiological saline, a Ringer solution or a buffer). The concentration of the solution or dispersion of the sample (pharmaceutically active ingredient) and the amount of albumin and/or globulin to be added to the solution or dispersion of the sample may be appropriately examined and determined. For example, when the sample is irinotecan hydrochloride, a solution or dispersion of the sample can be prepared by a known method. Alternatively, a commercial product having an irinotecan hydrochloride concentration of 20 mg/mL (Topotecin injection (Daiichi Pharmaceutical Co., Ltd.), Campto injection (Yakult Honsha Co., Ltd.)) may be used, and appropriate dilution ratio or concentration thereof may be determined according to the method described in Non-Patent Document 2. In the present invention, 20 mg/mL irinotecan hydrochloride solution is preferably diluted to 100 fold or more, and up to a concentration at which the endotoxin at a level of the specification limit can be detected, preferably to 3000 fold or less. However, the dilution ratio is not limited thereto.

When the sample (pharmaceutically active ingredient) is a taxane derivative, a solution or dispersion thereof can be prepared by a known method. Alternatively, a commercial product containing paclitaxel at a concentration of 5 mg/mL as a taxane derivative (Taxol injection (Bristol-Myers K.K.) or a commercial product containing docetaxel hydrate at a concentration of 40 mg/mL (Taxotere injection (sanofi-aventis K.K.) may be used, and appropriate dilution ratio or concentration thereof may be determined according to the method described in Non-Patent Document 2. When the taxane derivative is (−)-(1S,2S,3R,4S,5R,8R,9S,10R,13S)-4-acetoxy-2-benzoyloxy-9,10-[(1S)-2-(dimethylamino)ethylideneoxy]-5,20-epoxy-1-hydroxytax-11-en-13-yl(2R,3S)-3-(tert-butoxycarbonylamino)-3-(3-fluoro-2-pyridyl)-2-hydroxypropionate, 2 mg/ml solution thereof is preferably diluted to 16 fold or more, and up to a concentration at which the endotoxin at a level of the specification limit can be detected, preferably 1 to 200 fold or less. However, the dilution ratio is not limited thereto.

When the sample (pharmaceutically active ingredient) is timiperone, a solution or dispersion thereof can be prepared by a known method. Alternatively, a commercial product having a timiperone concentration of 2 mg/ml (Tolopelon injection (Daiichi Pharmaceutical Co., Ltd.)) may be used, and appropriate dilution ratio or concentration thereof may be determined according to the method described in Non-Patent Document 2. In the present invention, 2 mg/mL timiperone solution is preferably diluted to more than 8 fold, and up to a concentration at which the endotoxin at a level of the specification limit can be detected, preferably 9600 fold or less. However, the dilution ratio is not limited thereto.

In the endotoxin test according to the present invention, the pH of the solution or dispersion of the sample may be adjusted to 6.0 to 8.0.

In the present invention, while the amount of albumin and/or globulin to be added is appropriately examined and determined in consideration of the concentration of the solution or dispersion of the sample as described above, and preferably, 0.5 to 50 parts by weight of albumin and/or globulin is added to 1 part by weight of the sample. When the sample is camptothecin derivative, 1 to 50 parts by weight of albumin and/or globulin is preferably added to 1 part by weight of the camptothecin derivative. When the sample is timiperone, 0.5 to 7 parts by weight of albumin and/or globulin is preferably added to 1 part by weight of timiperone. When the sample is taxane derivative, 0.08 to 0.3 parts by weight of albumin and/or globulin is preferably added to 1 part by weight of the taxane derivative.

Also, the concentration of albumin and/or globulin to be added to the solution or dispersion of the sample is preferably lower than the concentration at which they act as an inhibitor of the reaction between lysate and endotoxin.

The lysate reagent according to the present invention may be a substance containing blood corpuscle extracts (lysate) of horseshoe crab (such as *Limulus polyphemus* or *Tachypleus tridentatus*). Such a reagent which can be used in the present invention is available from Daiichi Pure Chemicals, Co., Ltd., Wako Pure Chemical Industries, Ltd. or SEIKAGAKU CORPORATION, for example. While the lysate reagent may be used in an amount as described in an instruction manual of the lysate reagent or measurement devices, the amount is not limited thereto.

For the measurement of endotoxin in the present invention, any method may be used so long as the reaction between endotoxin and the lysate reagent can be detected and quantified. For example, the measurement may be performed in accordance with the method described in Non-Patent Document 2. Known endotoxin test methods include gel-clots techniques, which are based on gel formation by the reaction of a lysate reagent with endotoxin, turbidimetric techniques, which are based on the change in turbidity of the lysate reagent during gel formation, and chromogenic techniques, which are based on the development of color caused by hydrolysis of a synthetic substrate due to the reaction between endotoxin and a lysate reagent. However, any method may be used in the present invention without particular limitation.

For the measurement of endotoxin, commercially available endotoxin measurement devices may be used, which are available from CHARLES RIVER LABORATORIES JAPAN, INC., Wako Pure Chemical Industries, Ltd. and SEIKAGAKU CORPORATION, for example.

The reaction is preferably performed at 30 to 40° C., particularly at 37±1° C.

The endotoxin test method of the present invention is employed in a process for preparing an injection from a sample (pharmaceutically active ingredient) or for quality control thereof. In other words, the endotoxin test method of the present invention makes it possible to assess the presence or absence of endotoxin, and by providing a screening step of assessing the presence or absence of endotoxin, a solution or dispersion having an endotoxin concentration of less than the specification limit can be prepared. Accordingly, the present invention makes it possible to prepare an injection having an endotoxin concentration of less than the specification limit.

The present invention can be applied to any form of injections including aqueous injections, oil injections and freeze-dried injections. Generally, the specification limit of endotoxin in an injection is determined as follows based on the route of administration regardless of the form of the injection.

Endotoxin Limit=K/M

The value of K means the amount of endotoxin (EU (endotoxin unit)/kg) per 1 kg of body weight that is considered to elicit fever. Based on the route of administration of an injection, K=5 in the case of intravenous injection, K=2.5 in the case of intravenous injection (radiopharmaceutical) and K=0.2 in the case of intraspinal injection. The value of M means the maximum amount of an injection administered per 1 kg of body weight in an hour. The details are described in Section F-20, "4. Determining Endotoxin Limit" in Commentary of the Japanese Pharmacopoeia Fourteenth Edition, Hirokawa Publishing Co., 2001.

The present invention can be applied to a production process or for quality control of a pharmaceutical product in which endotoxin cannot be detected by the method described in Non-Patent Document 2 and to which albumin and/or globulin can be added for solving the problem. Accordingly, the subject sample of the test method and the process of the present invention should not be limited only to camptothecin derivatives, timiperone and taxane derivatives as exemplified in the above.

EXAMPLES

The present invention will be described with reference to Examples below, the present invention is not limited thereto.

Example 1

[Reagent]

(1) Sample

An irinotecan hydrochloride injection (concentration: 20 mg/mL; Topotecin injection (Daiichi Pharmaceutical Co., Ltd.)) appropriately diluted with water for injection was used.

(2) Endotoxin (Hereinafter ET)

Control standard ET (derived from *E. coli* strain 055:B5) appropriately diluted with water for injection was used.

(3) Human Serum Albumin (Hereinafter HSA) Solution

Human serum albumin (2%) solution appropriately diluted with water for injection was used.

(4) Lysate Reagent

Pyrogent 5000 (Daiichi Pure Chemicals, Co., Ltd.) dissolved in a dissolution buffer (Daiichi Pure Chemicals, Co., Ltd.) was used.

[Procedure]

The sample was diluted with water for injection and ET was added thereto to a predetermined concentration. After adding thereto an appropriate amount of the HSA solution and the lysate reagent and stirring, the ET concentration of the solution was measured using an endotoxin measurement device (Toxinometer ET-301 (Wako Pure Chemical Industries, Ltd.)) to determine the recovery rate of ET which had been added.

[Result]

The results are shown in Table 1 and Table 2. As shown in Table 1, in the irinotecan hydrochloride solution (concentration: 20 mg/mL) diluted appropriately, ET was not be detected using a conventional endotoxin test, while the ET recovery rate was improved and endotoxin test was conducted successfully by adding 1 to 50 parts by weight of HSA to 1 part by weight of irinotecan hydrochloride.

TABLE 1

| HSA concentration | | ET recovery rate (%) | | | | | |
|---|---|---|---|---|---|---|---|
| (mg/mL) | | 0 | 0.2 | 0.5 | 1 | 2 | 4 |
| irinotecan hydrochloride concentration (mg/mL) | 2 | became white (precipitation of pharmaceutical ingredient) | | | | | |
| | 0.2 | 53.4 | 121.2 | 100.6 | 98.6 | 66.3 | 36.6 |
| | 0.02 | 54.4 | 102.2 | 92.9 | 87.7 | 64.2 | 33.3 |

When HSA was added to the concentration of 0.1% based on the result shown in Table 1, the ET recovery rate was significantly improved when diluting the irinotecan hydrochloride solution (concentration: 20 mg/mL) to 100 to 3000 fold and endotoxin test was conducted successfully as shown in Table 2, whereby an endotoxin test was successful. According to Non-Patent Document 2, the test is effective when ET recovery rate is in the range of 50 to 200%.

TABLE 2

| dilution ratio (fold) | 100 | 500 | 1000 | 2000 | 3000 |
|---|---|---|---|---|---|
| irinotecan hydrochloride concentration (mg/mL) | 0.2 | 0.04 | 0.02 | 0.01 | 0.007 |
| HSA concentration (mg/mL) | | | 1 | | |
| ET recovery rate (%) | 100.5 | 141.3 | 123.9 | 109.2 | 91.2 |

Example 2

Three lots of irinotecan hydrochloride injections (available from Daiichi Pharmaceutical Co. Ltd., product name: Topotecin injection) were appropriately diluted and parts by weight of HSA was added to 1 part by weight of irinotecan hydrochloride. ET was detected in the same manner as in Example 1 to determine the recovery rate of ET which had been added. The results are shown in Table 3.

TABLE 3

| dilution ratio (fold) | | irinotecan hydrochloride concentration (mg/mL) | | | |
|---|---|---|---|---|---|
| | | 0.2<br>100 | 0.04<br>500 | 0.02<br>1000 | 0.01<br>2000 |
| HSA concentration (mg/mL) | | 1 | 0.2 | 0.01 | 0.005 |
| ET recovery rate (%) | lot A | 74.7 | 90.7 | 103.3 | 97.6 |
| | lot B | 84.4 | 105.2 | 107.2 | 94.1 |
| | lot C | 95.8 | 125.3 | 144.5 | 111.4 |

As is evident from Table 3, the ET recovery rate was very good. Thus, control of the preparation process and quality of the irinotecan hydrochloride injection has been achieved, and the process for preparing an irinotecan hydrochloride injection having an ET concentration of less than the specification limit could be provided.

Example 3

[Reagent]

(1) Sample
Water for injection was added to timiperone and timiperone was dissolved by adding thereto an appropriate amount of a 0.1 mol/mL hydrochloric acid solution to prepare 2 mg/mL timiperone solution. The timiperone solution was appropriately diluted and used.

(2) ET
Control standard ET (derived from *E. coli* UKT-B) appropriately diluted with water for injection was used.

(3) HSA Solution
Human serum albumin (2%) solution appropriately diluted with water for injection was used.

(4) Lysate Reagent
Limulus HS-J Test Wako (Wako Pure Chemical Industries, Ltd.) dissolved in a Tris-HCl buffer for ET detection (Wako Pure Chemical Industries, Ltd.) was used.

[Procedure]
The sample was diluted with water for injection and ET was added thereto to a predetermined concentration. After adding thereto the HSA solution to the concentration of 0.01% and the lysate reagent and stirring, the ET concentration of the solution was measured using an endotoxin measurement device (Toxinometer ET-201 (Wako Pure Chemical Industries, Ltd.)) to determine the recovery rate of ET which had been added. The experiment was performed in the same manner as described above except that pH was adjusted or sodium citrate was added so as to remove reaction interference factors in the endotoxin test instead of adding the HSA solution.

[Result]
The results are shown in Table 4 and Table 5.

TABLE 4

| dilution ratio (fold) | | 8 | 16 | 32 | 64 | 128 | 256 | 512 |
|---|---|---|---|---|---|---|---|---|
| ET recovery rate (%) | HSA added | became white | 96 | 100 | 91 | 82 | — | — |
| | HSA not added | 37 | 40 | 44 | 62 | 59 | 50 | 35 |

TABLE 5

| dilution ratio (fold) | | 1 | 10 | 100 | 1000 |
|---|---|---|---|---|---|
| ET recovery rate (%) | pH adjustment | 102* | 17 | 32 | 38 |
| | addition of sodium citrate | — | 17 | 20 | 40 |

*false positive due to timiperone precipitation

As shown in Table 4, when 0.5 to 7 parts by weight of HSA was added to 1 part by weight of timiperone, the ET recovery rate was significantly improved and endotoxin test was conducted successfully when diluting the 2 mg/mL timiperone solution to 16 fold or more. However, the endotoxin test was unsuccessful with pH adjustment or addition of sodium citrate which are known as a method of removing reaction interference factors.

Example 4

[Reagent]

(1) Sample
Appropriate amounts of water for injection and a 0.1 mol/mL hydrochloric acid solution were added to (−)-(1S,2S,3R,4S,5R,8R,9S,10R,13S)-4-acetoxy-2-benzoyloxy-9,10-[(1S)-2-(dimethylamino)ethylideneoxy]-5,20-epoxy-1-hydroxytax-11-en-13-yl(2R,3S)-3-(tert-butoxycarbonylamino)-3-(3-fluoro-2-pyridyl)-2-hydroxypropionate (hereinafter compound A) to prepare 2 mg/mL of compound A solution. The compound A solution was appropriately diluted with water for injection and used.

(2) ET
USP Reference Standard EC-6 (SEIKAGAKU CORPORATION) was used.

(3) HSA Solution
Human serum albumin (2%) solution appropriately diluted with water for injection was used.

(4) Lysate Reagent
A lysate reagent included in Kinetic-QCL Kit (Daiichi Pure Chemicals, Co., Ltd.) was used.

[Procedure]
The sample was diluted with water for injection and ET was added thereto to a predetermined concentration. After adding thereto an appropriate amount of the HSA solution and the lysate reagent and stirring, the ET concentration of the solution was measured using an endotoxin measurement device (ELx 808 Reader (Daiichi Pure Chemicals, Co., Ltd.) to determine the recovery rate of ET which had been added.

The results are shown in Table 6. In the compound A solution (concentration: 2 mg/mL) diluted appropriately, ET was not be detected using a conventional endotoxin test, while the ET recovery rate was improved and endotoxin test was conducted successfully by adding 0.08 to 0.3 parts by weight of HSA to 1 part by weight of the compound A.

TABLE 6

| dilution ratio (fold) | 4 | 8 | 16 | | | 32 | | | 64 |
|---|---|---|---|---|---|---|---|---|---|
| compounnd A concentration (mg/mL) | 0.5 | 0.25 | 0.125 | | | 0.0625 | | | 0.0312 |
| HSA concentration (mg/mL) | 0 | 0 | 0 | 0 | 0.02 | 0.01 | 0.005 | | 0 |
| ET recovery rate (%) | 0 | 0 | 15 | 23 | 87 | 84 | 78 | | 40 |

INDUSTRIAL APPLICABILITY

As expressly indicated in Examples described above, the endotoxin test method of the present invention makes it possible to detect and quantify endotoxin derived from gram-negative bacteria in a sample in which the endotoxin cannot be accurately detected or quantified by conventional test methods.

According to the present invention, a preparation process and quality control of an injection can be achieved without using a complicated pyrogen test, and a process for preparing an injection having an endotoxin concentration of less than the specification limit can be provided.

The invention claimed is:

1. A process for preparing an injection containing a camptothecin derivative, a timiperone or a taxane derivative and having an endotoxin concentration of less than a specification limit, the process comprising adding a lysate reagent to a solution or dispersion of the camptothecin derivative, the timiperone or the taxane derivative in the presence of albumin and/or globulin; assessing the presence or absence of endotoxin; and preparing the solution or dispersion in a form suitable for injection.

2. The process according to claim 1, wherein the albumin and/or globulin is human serum albumin.

3. The process according to claim 1, wherein the camptothecin derivative is irinotecan hydrochloride.

4. The process according to clam 1, wherein the solution or dispersion contains a camptothecin derivative.

5. The process according to claim 1, wherein the solution or dispersion contains a timiperone.

6. The process according to claim 1, wherein the solution or dispersion contains a taxane derivative.

7. The process according to claim 1, wherein the albumin and/or globulin is present in an amount of 0.5 to 50 parts by weight of the sample.

8. The process according to claim 1, wherein the albumin and/or globulin is present in an amount of 1 part by weight of the sample.

9. In a process for preparing an injection containing a camptothecin derivative, a timiperone or a taxane derivative and having an endotoxin concentration of less than a specification limit, the improvement comprising adding a lysate reagent to a solution or dispersion of the camptothecin derivative, the timiperone or the taxane derivative in the presence of albumin and/or globulin; and assessing the presence or absence of endotoxin.

10. The process according to claim 9, wherein the albumin and/or globulin is human serum albumin.

11. The process according to claim 9, wherein the camptothecin derivative is irinotecan hydrochloride.

12. The process according to clam 9, wherein the solution or dispersion contains a camptothecin derivative.

13. The process according to claim 9, wherein the solution or dispersion contains a timiperone.

14. The process according to claim 9, wherein the solution or dispersion contains a taxane derivative.

15. The process according to claim 9, wherein the albumin and/or globulin is present in an amount of 0.5 to 50 parts by weight of the sample.

16. The process according to claim 9, wherein the albumin and/or globulin is present in an amount of 1 part by weight of the sample.

17. A process for assessing the presence of absence of an endotoxin in a pharmaceutically acceptable injectable composition containing a camptothecin derivative, a timiperone or a taxane derivative and having an endotoxin concentration of less than a specification limit, the process comprising adding a lysate reagent to a solution or dispersion of the camptothecin derivative, the timiperone or the taxane derivative in the presence of albumin and/or globulin; and assessing the presence or absence of endotoxin.

18. The process according to claim 17, wherein the albumin and/or globulin is human serum albumin.

19. The process according to claim 17, wherein the camptothecin derivative is irinotecan hydrochloride.

20. The process according to clam 17, wherein the solution or dispersion contains a camptothecin derivative.

21. The process according to claim 17, wherein the solution or dispersion contains a timiperone.

22. The process according to claim 17, wherein the solution or dispersion contains a taxane derivative.

23. The process according to claim 17, wherein the albumin and/or globulin is present in an amount of 0.5 to 50 parts by weight of the sample.

24. The process according to claim 17, wherein the albumin and/or globulin is present in an amount of 1 part by weight of the sample.

* * * * *